US012616766B2

(12) United States Patent
Kawaguchi

(10) Patent No.: US 12,616,766 B2
(45) Date of Patent: May 5, 2026

(54) CLOSTRIDIODES DIFFICILE GROWTH INHIBITOR

(71) Applicant: Nutri Co., Ltd., Yokkaichi (JP)

(72) Inventor: Susumu Kawaguchi, Yokkaichi (JP)

(73) Assignee: Nutri Co., Ltd., Yokkaichi (JP)

( * ) Notice: Subject to any disclaimer, the term of this patent is extended or adjusted under 35 U.S.C. 154(b) by 771 days.

(21) Appl. No.: 17/802,611

(22) PCT Filed: Mar. 8, 2021

(86) PCT No.: PCT/JP2021/008920
§ 371 (c)(1),
(2) Date: Aug. 26, 2022

(87) PCT Pub. No.: WO2021/182377
PCT Pub. Date: Sep. 16, 2021

(65) Prior Publication Data
US 2023/0144328 A1     May 11, 2023

(30) Foreign Application Priority Data
Mar. 13, 2020     (JP) ................................. 2020-043740

(51) Int. Cl.
*A61L 2/18* (2006.01)

(52) U.S. Cl.
CPC ........... *A61L 2/18* (2013.01); *A61L 2300/232* (2013.01); *A61L 2300/30* (2013.01); *A61L 2300/404* (2013.01)

(58) Field of Classification Search
CPC ....................................................... A61L 2/18
See application file for complete search history.

(56) References Cited

U.S. PATENT DOCUMENTS

| | | |
|---|---|---|
| 2014/0037766 A1 | 2/2014 | Phillips et al. |
| 2016/0158295 A1 | 6/2016 | Afeyan et al. |
| 2019/0111168 A1 | 4/2019 | Baumler et al. |
| 2021/0046127 A1 | 2/2021 | Kim et al. |

FOREIGN PATENT DOCUMENTS

| | | |
|---|---|---|
| JP | 2002-540900 A | 12/2002 |
| JP | 2005-270735 A | 10/2005 |
| JP | 2007-320946 A | 12/2007 |
| JP | 2011-521937 A | 7/2011 |
| JP | 2019-515946 A | 6/2019 |
| KR | 10-2837762 B1 | 7/2025 |
| WO | 00/61201 A1 | 10/2000 |

(Continued)

OTHER PUBLICATIONS

English machine translation of JP 2007-320946 A; Dec. 2007 (Year: 2007).*

(Continued)

*Primary Examiner* — Sean E Conley
(74) *Attorney, Agent, or Firm* — Morgan, Lewis & Bockius LLP

(57) ABSTRACT

Provided is a growth inhibitor for *Clostridioides difficile*. A growth inhibitor for *Clostridioides difficile*, comprising killed *Enterococcus faecalis*. Also provided are a parenteral pharmaceutical preparation, a bactericide, a disinfectant, an antibacterial agent, a sanitizer or a detergent for inhibiting the growth of *Clostridioides difficile*.

21 Claims, 1 Drawing Sheet

(56)            References Cited

FOREIGN PATENT DOCUMENTS

| WO | 2005/087241 A1 | 9/2005 |
| WO | 2018/139503 A1 | 8/2018 |
| WO | 2019/078381 A1 | 4/2019 |
| WO | 2020/075637 A1 | 4/2020 |

OTHER PUBLICATIONS

International Search Report issued in corresponding International Patent Application No. PCT/JP2021/008920 dated Apr. 27, 2021.

Nakao et al., "Effects of Heat-killed Lactic Acid Bacteria Enterococcus faecalis on Life-threatening Antibiotic-resistant Bacteria in Animal Models," Journal of New Remedies & Clinics, 69 (3): 276-287 (2020) (see ISR).

Inatomi et al., "Effects of heat-killed Enterococcus faecalis T-110 supplementation on guy immunity, gut flora, and intestinal infection in naturally aged hamsters," PLOS One, 15 (12): e0240773 (2020).

Matsuo et al., "The Effect of a Heat-killed Lactic Acid Bacteria Enterococcus faecalis for Inhibiting the Proliferation of Clostridioides (Clostridium) Difficile," Japanese Pharmacology and Therapeutics, 48 (4): 721-725 (2020) (see English abstract).

Gu et al., "Protective Effects of Enterococcus Faecalis 2001 (EF 2001) against Radiation-induced Leukocytes Damage in Mice", Journal of Junshin Gakuen University, Faculty of Health Sciences , vol. 2 , Mar. 2013, pp. 55-61.

Office Action (with English Summary) dated Mar. 26, 2024, issued in corresponding Chinese Patent Application No. 202180015419.2.

Search Report issued in corresponding Singaporean Patent Application No. 11202252038E, dated Oct. 22, 2025.

Invitation to Respond to Written Opinion issued in corresponding Singaporean Patent Application No. 11202252038E, dated Oct. 25, 2025.

Written Opinion issued in corresponding Singaporean Patent Application No. 11202252038E, dated Oct. 25, 2025.

Office Action issued in corresponding Korean Patent Application No. 10-2022-7027329, dated Jan. 2, 2026.

* cited by examiner

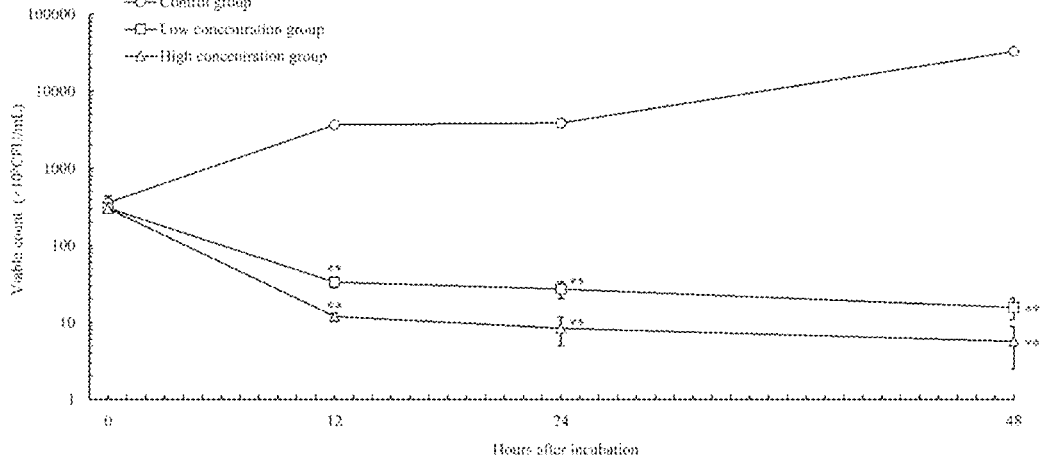

CLOSTRIDIODES DIFFICILE GROWTH INHIBITOR

TECHNICAL FIELD

The present invention relates to a growth inhibitor for *Clostridioides* (*Clostridium*) *difficile*.

BACKGROUND ART

*Clostridioides* (*Clostridium*) *difficile* infections (CDIs) often occur when the gastrointestinal flora is disrupted by use of antibiotics or some other reason. In most cases, development of CDIs is associated with use of antibiotics. Further susceptibility factors for developing CDIs include aging and presence of underlying diseases.

Most of CDIs are gastrointestinal infections, main symptoms of which are diarrhea and abdominal pain. CDIs are sometimes accompanied by fever and leukocytosis, occasionally leading to death due to toxic megacolon, ileus or gastrointestinal perforation if their symptoms become severer.

There are "carriers" of *Clostridioides difficile* who carry *C. difficile* in the gastrointestinal tract but are asymptomatic. A large number of such "carriers" are found among hospitalized patients to whom antibiotics are frequently administered. *C. difficile* is discharged with the stool of CDI patients and asymptomatic carriers, contaminates the environment including the fingers of health care workers and medical staff, and causes a problem of health-care-associated infection. Therefore, CDI is a common infection in health care sites where a number of elderly persons who need excretion care (such as exchange of diapers) are hospitalized and yet infection control (including appropriate use of antibiotics) is not adequately performed. However, in those medical institutions where antibiotics are abused or infection control is inadequate, the levels of concern and knowledge about CDI are so low that it often occurs that the disease is not diagnosed appropriately and its incidence seems apparently low: this is indeed a problematic situation.

Thus, medical institutions and elderly care facilities are in an environment where CDI easily becomes chronic and this had led to a discussion about the necessity for taking infection control measures.

PRIOR ART LITERATURE

Non-Patent Documents

Non-Patent Document No. 1: Basic science and clinical aspect of *C. difficile* infection,
Modern Media Vol. 56, No. 10, 2010 www.eiken.co.jp/modern_media/backnumber/pdf/MM1010_01.pdf

DISCLOSURE OF THE INVENTION

Problem for Solution by the Invention

It is an object of the present invention to provide a growth inhibitor for *Clostridioides difficile*.

Means to Solve the Problem

As a result of intensive efforts, the present inventors have found that killed *Enterococcus faecalis* can inhibit the growth of *Clostridioides difficile*; the present invention has been achieved based on this finding.

The gist of the present invention is as follows.
(1) A growth inhibitor for *Clostridioides difficile*, comprising killed *Enterococcus faecalis*.
(2) A parenteral pharmaceutical preparation for inhibiting the growth of *Clostridioides difficile*, comprising killed *Enterococcus faecalis*.
(3) A bactericide, disinfectant, antibacterial agent, sanitizer or detergent for inhibiting the growth of *Clostridioides difficile*, comprising killed *Enterococcus faecalis*.
(4) A medicine for external use, comprising killed *Enterococcus faecalis*.
(5) A hygiene product comprising killed *Enterococcus faecalis*.

Effect of the Invention

The present invention enables inhibition of the growth of *Clostridioides difficile*.

The present specification encompasses the contents of the specification and/or drawings disclosed in Japanese Patent Application No. 2020-43740 based on which the present application claims priority.

BRIEF DESCRIPTION OF THE DRAWINGS

FIG. 1 shows test results (viable cell count ($\times 10^3$ CFU/ml)) in Example 1. $\bigcirc$: Control group; $\square$: Low concentration group (test substance concentration: 0.64 mg/ml); $\Delta$: high concentration group (test substance concentration: 64 mg/ml). Significant difference compared with the control group (**: $p < 0.01$).

BEST MODES FOR CARRYING OUT THE INVENTION

Hereinafter, embodiments of the present invention will be described in more detail.

The present invention provides a growth inhibitor for *Clostridioides difficile*, comprising killed *Enterococcus faecalis*. The present invention also provides a method of inhibiting the growth of *Clostridioides difficile*, comprising using killed *Enterococcus faecalis*. Further, the present invention provides drugs comprising killed *Enterococcus faecalis*, for use in a method of inhibiting the growth of *Clostridioides difficile*.

*Enterococcus faecalis* is known as a lactic acid coccal bacterium having biological response modifier (BRM) activity (YAKUGAKU ZASSHI, 112:919-925, 1992; YAKUGAKU ZASSHI, 113:396-399, 1992; Journal of Animal Clinical Research, 3:11-20, 1994). *Enterococcus faecalis* EF-2001 strain is available from Nihon Berumu Co., Ltd. (2-14-3 Nagatacho, Chiyoda-ku, Tokyo).

*Enterococcus Faecalis*-2001 strain can be obtained from the stool of a normal person and has the following properties.

A Gram-positive coccus. Shape of colony (Trypto-Soya agar medium, 24-hour culture): 1.0-mm diameter, smooth, precise circle, white colony. Bacterial morphology: circular to oval (1.0×1.5 μm). Likely to form chains in liquid media. Non-spore-forming. Facultative anaerobic. Ferments glucose to produce lactic acid (final pH: 4.3). Non-gas-producing. Catalase-negative. Proliferates at 10 to 45° C. (the optimal temperature is 37° C.). Proliferates to pH 9.6, 6.5% NaCl, and 40% bile. Positive for 0.04% potassium tellurite. Positive for 0.01% tetrazolium. Positive for 0.1% methylene blue milk. Hydrolyzes arginine. Ferments amygdalin, cellobiose, fructose, galactose, glucose, glycerol, lactose, maltose, mannose, mannitol, ribose, salicin, sucrose, melicitose, and sorbitol to produce acids. Resistant at 60° C. for 30 minutes. Digests casein and gelatin. Decarboxylates tyrosine into tyramine. Lancefield antigen group: D. GC %: 35.0±1.0%.

*Enterococcus faecalis* may suitably be a killed bacterium, and the bacterium may be subjected to a destruction treatment (e.g., homogenization, enzyme treatment, or ultrasonication) or any other treatment such as heating or drying (e.g., freeze-drying or spray-drying). Viable *Enterococcus faecalis* may be killed by heating. Killed *Enterococcus faecalis* is expected to exhibit an intestinal immunity-activating effect. The particle size of the bacterial cell is typically 0.05 μm-50 μm, preferably 0.08-20 μm, more preferably 0.1-10 μm. The bacterium may be mixed with a diluent, and then a thickener may be added to form granules. It is recommended to select the diluent and thickener from materials approved for addition to foods and medicines.

Killed *Enterococcus faecalis* acts on the growth of *Clostridioides difficile* in a suppressive manner. By inhibiting the growth of *Clostridioides difficile*, it is possible to prevent and/or treat *Clostridioides difficile* infection. Killed *Enterococcus faecalis* can be used in a medicine as an active ingredient of a parenteral preparation. Further, killed *Enterococcus faecalis* can be used in a pharmaceutical preparation or quasi drug as an active ingredient of a bactericide. As an active ingredient of a disinfectant, killed *Enterococcus faecalis* can be used for sterilizing medical devices or for external application to human or animal skin. As an active ingredient of an antibacterial agent or sanitizer, killed *Enterococcus faecalis* can be used in hygiene products. Further, by using killed *Enterococcus faecalis* for washing human bodies, instruments, equipment, facilities, etc., it is possible to inhibit the growth of *Clostridioides difficile*. Therefore, the present invention provides a bactericide, disinfectant, antibacterial agent, sanitizer or detergent comprising killed *Enterococcus faecalis*, for inhibiting the growth of *Clostridioides difficile*. The present invention further provides a medicine for external use, comprising killed *Enterococcus faecalis*. Still further, the present invention provides a hygiene product comprising killed *Enterococcus faecalis*.

In the present invention, when sterilization, disinfection, bacterial eradication or washing is carried out using killed *Enterococcus faecalis*, the killed bacterium may be applied to the surface (skin, mucosa, etc.) of the body of human or non-human animal. Alternatively, killed *Enterococcus faecalis* may be either applied to the surface of instruments, equipment, facilities, etc. which may come into contact with the body of human or non-human animal, or sprayed or dispersed in the space where humans or non-human animals are breathing.

A bactericide, disinfectant, antibacterial agent, sanitizer or detergent comprising killed *Enterococcus faecalis* may be formulated into various dosage forms such as sprays (aerosols, pump sprays, etc.), transdermal patches (aqueous-type cataplasms, oily-type plasters, etc.), ointments, creams, gels, solid agents for external use, or liquids for external use (liniments, lotions, etc.), and conveniently used as a medicine for external use (pharmaceutical composition for external use), a quasi drug or a hygiene product.

Examples of bases which may be used for such formulations include, but are not limited to, the following materials: oily components such as hydrocarbons (petrolatum, liquid paraffin, etc.), higher fatty acids and esters thereof (adipic acid, myristic acid, palmitic acid, stearic acid and esters thereof, etc.), waxes (beeswax, lanolin, etc.), higher alcohols (cetanol, stearyl alcohol, etc.): aqueous components such as water, polyhydric alcohols (glycerin, 1,3-propanediol, propylene glycol, etc.), lower alcohols (ethanol, isopropanol, etc.): surfactants (glycerin stearate, sorbitan fatty acid esters, polyoxyethylene alcohol ethers, carboxylates, sulfuric ester salts, etc.), preservatives (p-hydroxy benzoates, etc.), antioxidants (sodium hydrogen sulfite, ascorbic acid, etc.), and pH adjusters (citric acid hydrate, lactic acid, acetic acid, etc.).

The content of killed *Enterococcus faecalis* in the formulation varies depending on the type of the formulation, and is typically 0.001 to 100% by mass and preferably 0.01 to 100% by mass.

The dose of killed *Enterococcus faecalis* may be any amount sufficient to confirm inhibitory effect on the growth of *Clostridioides difficile*, and it varies depending on the form of the formulation, the site of application, the age and body weight of the patient, the presence or absence of underlying disease in the patient, the type of the underlying disease, and so forth. In the case of an adult patient, for example, it is recommended to apply to the skin or the nasal or oral mucosa at a concentration of about 0.01 to 500 mg/ml, preferably about 0.05 to 300 mg/ml, more preferably about 0.1 to 100 mg/ml, in terms of the amount of killed *Enterococcus faecalis*, at a frequency of one to several (e.g., 2, 3, 4, or 5) times per day. When killed *Enterococcus faecalis* is applied to other than human or non-human animals, (for example, to the surface or space of instruments, equipment, facilities, etc.), the above described dose may also be used.

Killed *Enterococcus faecalis* may be added to gauze, absorbent cotton, alcohol swab, cotton swab, bandage, mask, gloves, adhesive plaster, surgical tape, bed & bath supplies (towels, sheets, etc.), wet wipes, wet towel, soap, coagulant for excrement, and the like.

A parenteral pharmaceutical preparation comprising killed *Enterococcus faecalis* may be formulated into various dosage forms such as agents for external application [sprays (e.g. aerosolss, pump sprays), transdermal patches (e.g. aqueous-type cataplasms, oily-type plasters, etc.), ointments, creams, gels, solid agents for external use, or liquids for external use (e.g. liniments, lotions)], injections, infusions, agents for ophthalmic use (e.g. eye drops, eye washes, ophthalmic ointments), suppositories, or the like and conveniently used as a medicine.

Examples of bases which may be used for agents for external application (such as sprays) include, but are not limited to, the following materials: oily components such as hydrocarbons (petrolatum, liquid paraffin, etc.), higher fatty acids and esters thereof (adipic acid, myristic acid, palmitic acid, stearic acid and esters thereof, etc.), waxes (beeswax, lanolin, etc.), higher alcohols (cetanol, stearyl alcohol, etc.): aqueous components such as water, polyhydric alcohols (glycerin, 1,3-propanediol, propylene glycol, etc.), lower alcohols (ethanol, isopropanol, etc.): surfactants (glycerin stearate, sorbitan fatty acid esters, polyoxyethylene alcohol ethers, carboxylates, sulfuric ester salts, etc.), preservatives (p-hydroxy benzoates, etc.), antioxidants (sodium hydrogen sulfite, ascorbic acid, etc.), and pH adjusters (citric acid hydrate, lactic acid, acetic acid, etc.). Topical agents may be suitably applied to the skin or the nasal or oral mucosa.

Injections and infusions may be formulated using solvents [aqueous solvents (e.g. distilled water, physiological saline, Ringer's solution), non-aqueous solvents (e.g. ethanol, propylene glycol, vegetable oil)], dissolution aids (e.g. glutamic acid, aspartic acid, Polysorbate 80), preservatives (e.g. benzalkonium chloride, benzethonium chloride), stabilizers (e.g. sulfites, sodium pyrosulfite), emulsifiers/suspending agents (e.g. lecithin, aluminum monostearate), buffers (e.g. acids, alkalis, citrates), coloring agents and the like. Formulations may be sterilized at the final step of their preparation or may be prepared by aseptic techniques. Alternatively, aseptic freeze-dried products may be prepared and dissolved in aseptic distilled water for injection or other solvents before use. Injections and infusions are applied to the body either intradermally or via skin or mucosa. They may also be applied via nasal cavity. Routes of administration include intradermal, subcutaneous, intramuscular, intravenous and intranasal.

Eye drops may be formulated using solvents [aqueous solvents (e.g. sterilized purified water, physiological saline), non-aqueous solvents (e.g. ethanol, propylene glycol, vegetable oil)], buffers, isotonic agents, preservatives (e.g. methyl-p-hydroxybenzoate, ethyl-p-hydroxybenzoate, benzalkonium chloride, benzethonium chloride), viscous agents (e.g. methyl cellulose, chondroitin sulfate), suspending agents (e.g. non-ionic surfactants), coloring agents and the like.

Eye washes may be prepared using physiological saline, boric acid solution, benzethonium chloride, buffers and the like.

Eye ointments may be formulated using paraffin, liquid paraffin or the like as a base and, if necessary, by further adding preservatives, stabilizers, etc.

Suppositories may be formulated using bases [oleaginous bases (e.g. cocoa butter, coconut oil, palm kernel oil), water-soluble bases (e.g. glycerinated gelatin, macrogol)], surfactants (e.g. lecithin, cholesterol) and the like.

The content of killed *Enterococcus faecalis* in the pharmaceutical formulation varies depending on the type of the formulation, and is typically 0.001 to 100% by mass and preferably 0.01 to 100% by mass.

The dose of killed *Enterococcus faecalis* may be any amount sufficient to confirm inhibitory effect on the growth of *Clostridioides difficile*, and it varies depending on the form of the formulation, the site of application, the age and body weight of the patient, the presence or absence of underlying disease in the patient, the type of the underlying disease, and so forth. In the case of an adult patient, for example, it is recommended to administer at a concentration of about 0.01 to 500 mg/ml, preferably about 0.05 to 300 mg/ml, more preferably about 0.1 to 100 mg/ml, in terms of the amount of killed *Enterococcus faecalis*, at a frequency of one to several (e.g., 2, 3, 4, or 5) times per day.

It is also possible to prepare antibacterial products (such as antibacterial towels, antibacterial plastic tableware, antibacterial toys, antibacterial PC-related products, antibacterial stationery, etc.) by coating or rubbing with the antibacterial agent of the present invention.

EXAMPLES

Hereinafter, the present invention will be described in detail based on Examples. The present invention is not limited to these Examples.

[Example 1] Test to Confirm the Action of Lactic Acid Bacterium EF-2001 Strain on *C. difficile* Summary The action of the lactic acid bacterium on *C. difficile* was examined.

To 1 ml of inoculum, 0.65 ml of low concentration (1.63 mg/ml) or high concentration (163 mg/ml) lactic acid bacterium suspension was added. *C. difficile* was cultured anaerobically with the concentration of the lactic acid bacterium being at 0.64 mg/ml or 64 mg/ml. Viable cell count was taken at 12 hours, 24 hours and 48 hours of culture.

Whether the concentration condition of the lactic acid bacterium was low (0.64 mg/ml) or high (64 mg/ml), viable cell count of *C. difficile* decreased significantly at 12 hours, 24 hours and 48 hours of culture, as compared to the control group. From these results, it was presumed that the lactic acid bacterium would act on the growth of *C. difficile* in an inhibitory manner.

Materials and Methods

1. Test Substance 1.1. Test Substance

Name: LACTIC ACID BACTERIA POWDER EF-2001 (Nihon Berumu Co., Ltd.) (heat-killed *E. faecalis*, 500 nm=0.5 μm in diameter)

Properties: Yellow-brown powder

Storage conditions: Room temperature (18.0-28.0° C.), light-shielded, moisture-proof Storage site: Storage cabinet in the test substance storage room of the testing facility 2. Administration Sample 2.1. Preparation Method for Test Substance The necessary amount of lactic acid bacteria powder EF-2001 was weighed (electronic balance: XP205DR, Mettler-Toledo Co., Ltd.) and suspended in GAM broth (see 15.3.4.) to prepare a suspension of 500 mg/ml. This 500 mg/ml suspension was diluted with GAM broth to give concentrations of 163 mg/ml and 1.63 mg/ml. Since the lactic acid bacteria powder precipitates, it was stirred well enough to be kept suspended. Preparation was made just before use.

3. Pathogenic Microorganism 3.1. Strain Used

*Clostridioides* (*Clostridium*) *difficile* (ATCC43255, hereinafter referred to as "*C. difficile*")

3.2. Storage Conditions

Cryopreserved in an Ultra-cold freezer (controlled temperature: −80° C., MDF-394AT, Sanyo Electric Co., Ltd.) until use.

3.3. Reagents (1) GAM agar medium (Nissui Pharmaceutical Co., Ltd.)

(2) GAM broth medium (Nissui Pharmaceutical Co., Ltd.)

(3) Physiological saline (Otsuka Pharmaceutical Plant, Inc.)

3.4. Preparation of GAM Broth

GAM broth powder was weighed in 29.5 g and suspended in 500 ml of water for injection (Otsuka Pharmaceutical Plant, Inc.). The resultant suspension was autoclaved with LSX-500 (TOMY SEIKO Co., Ltd.) at 115° C. for 15 minutes and then stored under refrigerating conditions.

3.5. Preculture

The preserved strain of *C. difficile* was thawed and inoculated into GAM agar medium. The resultant medium was transferred into a deoxidant-filled anaerobic jar, and then cultured for 5 days in an incubator (ILE800, Yamato Scientific Co., Ltd.) set at 37° C. After culture, colonies were collected and added to GAM broth medium, which was transferred into a deoxidant-filled anaerobic jar and cultured for 2 days in an incubator set at 37° C. The resultant culture broth served as an inoculation stock solution.

3.6. Preparation of a Liquid Bacterial Inoculum and Taking of Viable Cell Count

The stock solution diluted 10-folds with physiological saline was used as a liquid bacterial inoculum.

Confirmation of viable cell count was performed as follows. Briefly, an aliquot of liquid bacterial inoculum was taken, diluted appropriately with physiological saline, and smeared on GAM agar medium. Then, the medium was transferred into a deoxidant-filled anaerobic jar and cultured for 5 days in an incubator set at 37° C. The number of colonies after culture was counted with a handy colony counter (CC-1, Azwan Co., Ltd.), and the number of viable bacterial cells contained in 1 ml of the liquid bacterial inoculum was calculated. As a result, the concentration of the liquid bacterial inoculum was $2.8 \times 10^5$ CFU/mL.

The remaining liquid bacterial inoculum after use was autoclaved (LSX-500, TOMY SEOKO Co., Ltd.) at 121° C. for 15 minutes and discarded.

4. Testing Method 4.1. Growth Inhibition Test 4.1.1. Description of Test Groups

| Group No. | Test Group | Concentration of Test Substance (mg/ml) | Concentration of C. difficile Inoculum (CFU/ml) |
|---|---|---|---|
| 1 | Control | 0* | $1.7 \times 10^5$ |
| 2 | Low concentration | 0.64 | $1.7 \times 10^5$ |
| 3 | High concentration | 64 | $1.7 \times 10^5$ |

Indicated are the final concentrations after mixing.
*GAM broth was added.

4.1.2. Testing Method

To 1 ml of the liquid bacterial inoculum in a test tube, the prepared sample suspensions (1.63 mg/ml and 163 mg/ml) were each added in 0.65 ml. Test tubes were placed in a deoxidant-filled anaerobic jar, and C. difficile was cultured in an incubator set at 37° C. At the beginning of culture and at 12 hours, 24 hours and 48 hours of culture, the test tubes were taken out. An aliquot of culture broth was taken, and this culture broth itself or an appropriately diluted culture broth was smeared on CCFA medium (Nippon Becton Dickinson Company, Ltd.), followed by 5-day anaerobic culture in an incubator set at 37° C. The number of colonies after culture was counted with a handy colony counter, and the number of viable bacterial cells was calculated. As a control, GAM broth was used instead of the sample suspension. The number of samples was 5.

5. Summary of Results

As regards viable cell count, mean and standard error were calculated.

For significance test, Wilcoxon rank sum test was used for control group vs test groups on viable cell count.

A hazard rate of 5% was considered significant, and separate indications were given for a hazard rate less than 5% and a hazard rate less than 1%.

A commercially available statistical program (SAS system: SAS Institute Japan) was used for the statistical analyses.

Test Results

Test results are shown in Table 1, Appendix 1-1 to 1-3 and FIG. 1.

The viable cell count of C. difficile in the control group was $360.0 \pm 75.9$ ($\times 10^3$ CFU/ml) at the beginning of culture, $3680.0 \pm 239.6$ ($\times 10^3$ CFU/ml) at 12 hours of culture, $3880.0 \pm 475.8$ ($\times 10^3$ CFU/ml) at 24 hours of culture, and $33020.0 \pm 2267.5$ ($\times 10^3$ CFU/ml) at 48 hours of culture.

The viable cell count of C. difficile in the low concentration group was $306.0 \pm 22.7$ ($\times 10^3$ CFU/ml) at the beginning of culture, $33.2 \pm 4.9$ ($\times 10^3$ CFU/ml) at 12 hours of culture, $27.1 \pm 6.7$ ($\times 10^3$ CFU/ml) at 24 hours of culture, and $15.7 \pm 4.9$ ($\times 10^3$ CFU/ml) at 48 hours of culture. Compared to the control group, a significant decrease in the number of viable bacterial cells was observed at 12 hours, 24 hours and 48 hours of culture.

The viable cell count of C. difficile in the high concentration group was $300.0 \pm 22.1$ ($\times 10^3$ CFU/ml) at the beginning of culture, $12.0 \pm 1.1$ ($\times 10^3$ CFU/ml) at 12 hour of culture, $8.4 \pm 3.4$ ($\times 10^3$ CFU/ml) at 24 hours of culture, and $5.7 \pm 3.2$ ($\times 10^3$ CFU/ml) at 48 hours of culture. Compared to the control group, a significant decrease in the number of viable bacterial cells was observed at 12 hours, 24 hours and 48 hours of culture.

DISCUSSION

The action of the lactic acid bacterium on C. difficile was examined by taking the viable cell count over time.

Whether the concentration condition of the lactic acid bacterium was low (0.64 mg/ml) or high (64 mg/ml), viable cell count of C. difficile decreased significantly at 12 hours, 24 hours and 48 hours of culture, as compared to the control group. From these results, it was presumed that the lactic acid bacterium acts on the growth of C. difficile in an inhibitory manner.

TABLE 1

| | Viable count | | |
|---|---|---|---|
| Group | Control | Low concentration | High concentration |
| Number of samples Hours after incubation | 5 | 5 | 5 |
| 0 | $360.0 \pm 75.9$ | $306.0 \pm 22.7$ | $300.0 \pm 22.1$ |
| 12 | $3680.0 \pm 239.6$ | $33.2 \pm 4.0$ ** | $12.0 \pm 1.1$ ** |
| 24 | $3880.0 \pm 475.8$ | $27.1 \pm 6.7$ ** | $8.4 \pm 3.4$ ** |
| | $33020.0 \pm 22675$ | $15.7 \pm 4.9$ ** | $5.7 \pm 3.2$ ** |

Each value shows mean ($\times 10^3$ CFU/mL) ± S.E.

Significantly different from the control group (**: $p < 0.01$).

APPENDIX 1-1

| | Individual viable count Control group | | | |
|---|---|---|---|---|
| Sample | Hours after incubation | | | |
| No. | 0 | 12 | 24 | 48 |
| 1 | 660.0 | 4500.0 | 5200.0 | 24200.0 |
| 2 | 310.0 | 3200.0 | 2600.0 | 36900.0 |
| 3 | 250.0 | 3200.0 | 3000.0 | 35700.0 |
| 4 | 310.0 | 3700.0 | 4200.0 | 34500.0 |
| 5 | 270.0 | 3800.0 | 4400.0 | 33800.0 |
| Number of samples | 5 | 5 | 5 | 5 |
| Mean | 360.0 | 3680.0 | 3880.0 | 33020.0 |
| S.E. | 75.9 | 239.6 | 475.8 | 2267.5 |

Unit: $\times 10^3$ CFU/mL.

APPENDIX 1-2

Individual viable count
Low concentration group

| Sample No. | Hours after incubation | | | |
|---|---|---|---|---|
| | 0 | 12 | 24 | 48 |
| 1 | 340.0 | 33.0 | 41.0 | 13,0 |
| 2 | 370.0 | 33.0 | 1.7 | 31.0 |
| 3 | 240.0 | 17,0 | 33.0 | 0,5 |
| 4 | 280.0 | 35.0 | 31.0 | 15.0 |
| 5 | 300.0 | 48.0 | 29.0 | 19.0 |
| Number of samples | 5 | 5 | 5 | 5 |
| Mean | 306.0 | 33.2 | 27.1 | 15.7 |
| S.B. | 22.7 | 4.9 | 6.7 | 4.9 |
| Significance | NS | ** | ** | ** |
| Statistical method | WL | WL | WL | WI |

Unit: ×10³ CFU/mL.
Significantly different from the control group (**: p < 0.01).
NS: Not significantly different from the control group.
WL: Analysis by Wilcoxon's test.

APPENDIX 1-3

Individual viable count
High concentration group

| Sample No. | Hours after incubation | | | |
|---|---|---|---|---|
| | 0 | 12 | 24 | 48 |
| 1 | 340.0 | 13.0 | 0.4 | 0.5 |
| 2 | 290.0 | 9.0 | 0.4 | 0.4 |
| 3 | 240.0 | 13.0 | 15.0 | 0.5 |
| 4 | 360.0 | 10.0 | 10.0 | 15.0 |
| 5 | 270.0 | 15.0 | 16.0 | 12.0 |
| Number of samples | 5 | 5 | 5 | 5 |
| Mean | 300.0 | 12.0 | 8.4 | 5.7 |
| S.E. | 22.1 | 1.1 | 3.4 | 3.2 |
| Significance | NS | ** | ** | ** |
| Statistical method | WL | WI | | WL |

Unit: ×10³ CFU/mL.
Significantly different from the control group (**: p<0.01).
NS: Not significantly different from the control group.
WL: Analysis by Wilcoxon's test.

[Product Example 1] Sanitizer Liquid, Antibacterial
Spray and Sanitizing Wipes

A sanitizer liquid was prepared according to the following formula.

Lactic acid bacteria powder EF-2001 (Nihon
Berumu Co., Ltd.) (heat-killed *E. faecalis,* 500
nm=0.5 μm in diameter): 0.6% by mass          (Formula)
Glycerin: 0.05% by mass
Caprylic acid monoglyceride: 0.50% by mass
Ethanol: 50% by mass
Purified water: q. s.
Total 100% by mass The above-indicated solution was filled in a commercially available, pump-type spray container to prepare an antibacterial spray. The same solution was soaked in gauze or tissue paper to prepare sanitizing wipes.

All publications, patents and patent applications cited herein are incorporated herein by reference in their entirety.

INDUSTRIAL APPLICABILITY

The present invention is applicable to prevention and/or treatment of *Clostridioides difficile* infection, as well as to other uses including sterilization, disinfection, sanitizing and washing of the bacterium.

The invention claimed is:

1. A method of reducing growth of *Clostridioides difficile,* the method comprising applying killed *Enterococcus faecalis* to an object, wherein the object is an antibacterial product comprising at least one selected from the group consisting of antibacterial towels, antibacterial plastic tableware, antibacterial toys, antibacterial PC-related products, and antibacterial stationery; or the object comprises at least one selected from the group consisting of gauze, absorbent cotton, alcohol swab, cotton swab, bandage, mask, gloves, adhesive plaster, surgical tape, bed & bath supplies, wet wipes, wet towel, soap, and coagulant for excrement.

2. The method according to claim 1, wherein the killed *Enterococcus faecalis* is prepared as a liquid suspension.

3. The method according to claim 2, wherein the liquid suspension comprises 0.6% by mass or more of the killed *Enterococcus faecalis.*

4. The method according to claim 2, wherein the liquid suspension further comprises at least one selected from the group consisting of glycerin, caprylic acid monoglyceride, ethanol, and purified water.

5. The method according to claim 2, wherein the liquid suspension is used as a spray.

6. The method according to claim 2, wherein the liquid suspension is soaked in an absorbent material to prepare a sanitizing wipe.

7. The method according to claim 1, wherein the killed *Enterococcus faecalis* is EF-2001 strain.

8. The method according to claim 1, wherein the killed *Enterococcus faecalis* is prepared as a bactericide, a disinfectant, an antibacterial agent, a sanitizer, or a detergent.

9. The method according to claim 1, wherein the killed *Enterococcus faecalis* is prepared as an agent comprising 0.6% by mass or more of the killed *Enterococcus faecalis.*

10. A method of reducing growth of *Clostridioides difficile,* the method comprising applying killed *Enterococcus faecalis,* wherein applying the killed *Enterococcus faecalis* comprises externally administering a pharmaceutically effective amount of the killed *Enterococcus faecalis* to a subject in need thereof.

11. The method according to claim 10, wherein the subject is a human.

12. The method according to claim 10, wherein the killed *Enterococcus faecalis* is administered topically.

13. The method according to claim 10, wherein the killed *Enterococcus faecalis* is prepared as a transdermal patch.

14. The method according to claim 10, wherein the killed *Enterococcus faecalis* is prepared as an ointment, a gel, or a cream.

15. The method according to claim 10, wherein the killed *Enterococcus faecalis* is prepared as a liquid suspension.

16. The method according to claim 15, wherein the liquid suspension comprises 0.6% by mass or more of the killed *Enterococcus faecalis.*

17. The method according to claim 15, wherein the liquid suspension further comprises at least one selected from the group consisting of glycerin, caprylic acid monoglyceride, ethanol, and purified water.

18. The method according to claim 15, wherein the liquid suspension is used as a spray.

19. The method according to claim 15, wherein the liquid suspension is soaked in an absorbent material to prepare a sanitizing wipe.

20. The method according to claim 10, wherein the killed *Enterococcus faecalis* is EF-2001 strain.

21. The method according to claim 10, wherein the killed *Enterococcus faecalis* is prepared as an agent comprising 0.6% by mass or more of the killed *Enterococcus faecalis*.

* * * * *